(12) United States Patent
Min et al.

(10) Patent No.: US 8,287,459 B2
(45) Date of Patent: Oct. 16, 2012

(54) INTERPOLATING LEFT VENTRICULAR PRESSURES

(75) Inventors: Xiaoyi Min, Thousand Oaks, CA (US); Gene A. Bornzin, Simi Valley, CA (US)

(73) Assignee: Pacesetter, Inc., Sylmar, CA (US)

( * ) Notice: Subject to any disclaimer, the term of this patent is extended or adjusted under 35 U.S.C. 154(b) by 961 days.

(21) Appl. No.: 12/266,420

(22) Filed: Nov. 6, 2008

(65) Prior Publication Data

US 2010/0113944 A1    May 6, 2010

(51) Int. Cl.
*A61B 5/02* (2006.01)
*A61B 5/04* (2006.01)

(52) U.S. Cl. ........ 600/486; 600/485; 600/494; 600/501; 600/505; 600/508; 600/509; 600/513; 600/516; 600/517; 600/528; 607/18; 607/122; 607/123

(58) Field of Classification Search ................ 607/9, 17, 607/18, 19, 36, 119, 121, 122, 123; 600/485, 600/486, 504, 508, 509, 513, 518, 526–528, 600/494, 501, 505, 516, 517
See application file for complete search history.

(56) References Cited

U.S. PATENT DOCUMENTS

| | | | |
|---|---|---|---|
| 6,610,018 B1 * | 8/2003 | McIntyre | 600/485 |
| 6,869,404 B2 * | 3/2005 | Schulhauser et al. | 600/528 |
| 7,448,999 B1 * | 11/2008 | Karicherla et al. | 600/486 |
| 2010/0114230 A1 * | 5/2010 | Audit et al. | 607/18 |

\* cited by examiner

*Primary Examiner* — Gail R Gabel

(57) ABSTRACT

Exemplary techniques and systems for interpolating left ventricular pressures are described. One technique interpolates pressures within the left ventricle from blood pressures gathered without directly sensing blood pressure in the left ventricle.

23 Claims, 6 Drawing Sheets

INTERPOLATING LEFT VENTRICULAR PRESSURES

FIELD OF THE INVENTION

The subject matter presented herein generally relates to cardiac health and conversely heart failure as detected from interpolated left ventricular pressures.

BACKGROUND

Heart failure is a condition in which the heart is unable to pump enough blood in a forward direction to sustain normal bodily functions. The heart primarily accomplishes the forward movement of blood via the left ventricle. Accordingly, information about the functionality of the left ventricle is very useful for determining cardiac health. One useful indicator of the left ventricular functionality is blood pressures within the left ventricle. Unfortunately, left ventricular blood pressures are difficult to obtain.

SUMMARY

Exemplary techniques and systems for interpolating left ventricular pressures are described. One technique interpolates pressures within the left ventricle from blood pressures gathered without directly sensing blood pressure in the left ventricle.

Another technique senses blood pressures upstream and downstream of a patient's left ventricle. This technique also interpolates the patient's left ventricle pressures from the upstream and downstream pressures.

An exemplary system includes a mechanism operable to monitor aortic pressure of a patient and a mechanism operable to monitor left atrial pressure of the patient. The system further includes a mechanism operable to monitor cardiac valve events and a mechanism operable to interpolate left ventricle pressure from the aortic pressure, the left atrial pressure, and the cardiac valve events.

BRIEF DESCRIPTION OF THE DRAWINGS

Features and advantages of the described implementations can be more readily understood by reference to the following description taken in conjunction with the accompanying drawings. In the description that follows, like numerals or reference designators will be used to reference like parts or elements wherever feasible.

DETAILED DESCRIPTION

Overview

Various exemplary techniques, methods, devices, systems, etc., described herein pertain to interpolating left ventricular pressure. In many scenarios directly sensing pressures within the left ventricle may not be practical. The present implementations allow thoracic pressures to be interpolated or estimated from available cardiac related data, such as pressure data sensed upstream and/or downstream from the left ventricle. For instance, some implementations obtain upstream pressures from the left atrium and downstream pressures from the aorta. The left ventricle undergoes a repeating hemodynamic pressure cycle as blood enters the left ventricle from the left atrium and is forced by the contraction of the left ventricle into the aorta. The present concepts recognize that the left ventricular pressure is generally equivalent to (or can be interpolated from) pressures in the left atrium for a portion of the left ventricle's pressure cycle when the mitral valve is open. Stated another way, left atrial pressures offer a surrogate for left ventricular pressures when the open mitral valve fluidly connects the two chambers. Similarly, when the aortic valve is open, pressures within the aorta offer a surrogate for left ventricular pressures. Further, left ventricular pressure during the remaining periods of its pressure cycle can be interpolated from the available pressure data such as by employing curve extension techniques. Some implementations detect opening and/or closing of the mitral and/or aortic valves from various cardiac-related data. The detected mitral and aortic valve opening and closing offers a guidepost as to when left ventricular pressure converges with and diverges from left atrial and/or aortic pressures. The interpolated left ventricular data can be utilized to diagnose the patient's cardiac health and to generate a responsive patient therapy(s).

Exemplary IMD

The techniques described below can be implemented in connection with any implantable medical device (IMD) that is configured or configurable to sense cardiac data and/or to provide cardiac therapy.

Figure 1:
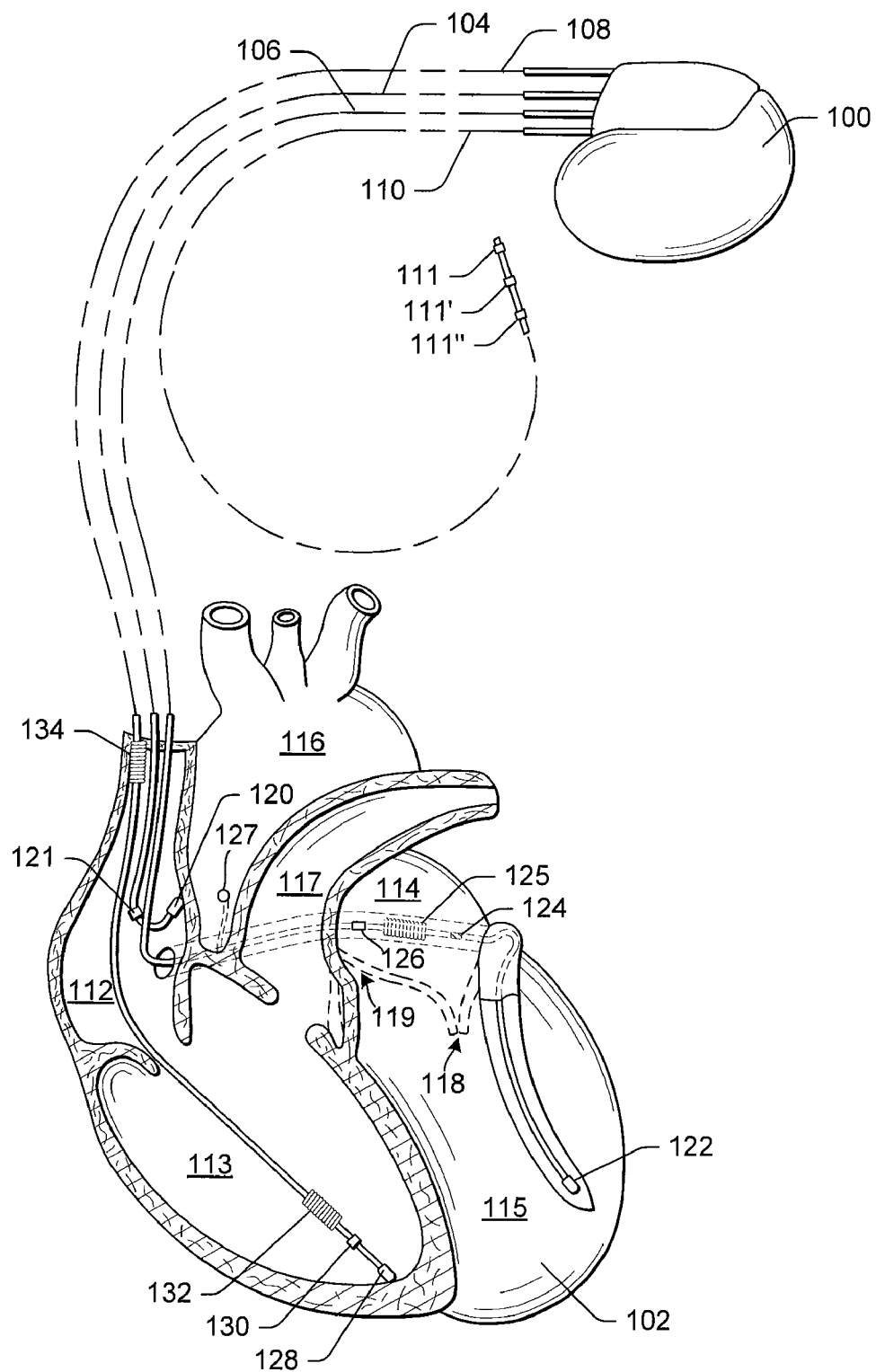
FIG. 1 is a simplified diagram illustrating an exemplary implantable medical device (IMD) operable to interpolate left ventricular pressure in accordance with one implementation.

FIG. 1 shows an exemplary IMD 100 in electrical communication with a patient's heart 102 by way of three leads 104, 106, 108, suitable for delivering multi-chamber stimulation and shock therapy.

The leads 104, 106, 108 are optionally configurable for delivery of stimulation pulses suitable for stimulation of autonomic nerves, non-myocardial tissue, other nerves, etc. In addition, IMD 100 includes a fourth lead 110 having, in this implementation, three electrodes 111, 111', 111" suitable for stimulation of autonomic nerves, non-myocardial tissue, other nerves, etc. For example, this lead may be positioned in and/or near a patient's heart or near an autonomic nerve within a patient's body and remote from the heart. In another example, the fourth lead can be configured to sense the phrenic nerve and/or activation of the diaphragm.

For purposes of discussion, the heart's right atrium, right ventricle, left atrium, and left ventricle, are designated as 112, 113, 114, and 115, respectively. Also, specifically designated are the aorta 116, pulmonary artery 117, mitral valve 118, and aortic valve 119 (partially occluded in the drawing). Blood returning from the lungs into the left atrium 114 is pumped downstream into the left ventricle 115 through mitral valve 118. The mitral valve closes when the left ventricle contracts thereby preventing the blood from flowing back upstream. Instead, contraction of the left ventricle increases pressures within the left ventricle until the aortic valve opens and blood is forced downstream into the aorta 116. Contraction of the left ventricle prior to opening of the aortic valve is often referred to as isovolumic contraction of the left ventricle.

The functionality of the left ventricle 115, such as the blood pressures of the left ventricle, are valuable indicators of cardiac health. However, direct sensing of pressures within the left ventricle is not readily accomplished and/or may not be desired due to associated complications. The present implementations, can sense blood pressures upstream and/or downstream from the left ventricle, such as in the left atrium 114 and/or the aorta 116. The implementations can also concurrently track mitral and aortic valve events (i.e., opening and closing of the mitral valve and aortic valves). Briefly stated, left ventricle pressures can be interpolated from upstream and/or downstream pressures and the concurrent mitral and/or aortic valve events. For instance, when the left atrium 114 is contracting and the mitral valve is open, fluid pressures within the left atrium and the left ventricle should generally approach equivalency consistent with the principles of hemodynamics. Similarly, when the left ventricle is contracting and the atrial valve 118 is open, downstream blood pressure, such as in aorta 116 should approach equivalency with the pressure of the left ventricle.

The right atrial lead 104, as the name implies, is positioned in and/or passes through a patient's right atrium 112. The right atrial lead 104 optionally senses atrial cardiac signals and/or provides right atrial chamber stimulation therapy. As shown in FIG. 1, the IMD 100 is coupled to an implantable right atrial lead 104 having, for example, an atrial tip electrode 120, which typically is implanted in the patient's right atrial appendage. The lead 104, as shown in FIG. 1, also includes an atrial ring electrode 121. Of course, the lead 104 may have other electrodes as well. For example, the right atrial lead optionally includes a distal bifurcation having electrodes suitable for stimulation of autonomic nerves, non-myocardial tissue, other nerves, etc. In an alternative configuration, lead 110 can be replaced with a mechanism for connecting the IMD to various other devices, such as various pressure sensors. For example, the mechanism can facilitate connecting IMD 100 to a drug pump for dispensing drugs into the patient in accordance with instructions received from the IMD. In another example, lead 110 can be connected to a pressure sensor positioned proximate the aorta or an artery supplied by the aorta. In still another case, lead 110 can be connected to a device that functions to detect cardiac sounds. The skilled artisan should recognize various other configurations that may be employed which are consistent with the principles described above and below.

To sense atrial cardiac signals, ventricular cardiac signals and/or to provide multi-site pacing therapy, particularly on the left side of a patient's heart, the IMD 100 is coupled to a coronary sinus lead 106 designed for placement in the coronary sinus and/or tributary veins of the coronary sinus. Thus, the coronary sinus lead 106 is optionally suitable for positioning at least one distal electrode adjacent to the left ventricle 115 and/or additional electrode(s) adjacent to the left atrium 114. In a normal heart, tributary veins of the coronary sinus include, but may not be limited to, the great cardiac vein, the left marginal vein, the left posterior ventricular vein, the middle cardiac vein, and the small cardiac vein.

Accordingly, an exemplary coronary sinus lead 106 is optionally designed to receive atrial and ventricular cardiac signals and to deliver left ventricular pacing therapy using, for example, at least a left ventricular tip electrode 122, left atrial pacing therapy using at least a left atrial ring electrode 124, and shocking therapy using at least a left atrial coil electrode 125. In this case, lead 106 is also connected to pressure sensors 126, 127 positioned in and for obtaining blood pressures from left atrium 114 and aorta 116, respectively. Various types of pressure sensors and use of the pressure data supplied by these pressures sensors is described in more detail below.

The coronary sinus lead 106 further optionally includes electrodes for stimulation of autonomic nerves. Such a lead may include pacing and autonomic nerve stimulation functionality and may further include bifurcations or legs. For example, an exemplary coronary sinus lead includes pacing electrodes capable of delivering pacing pulses to a patient's left ventricle and at least one electrode capable of stimulating an autonomic nerve. An exemplary coronary sinus lead (or left ventricular lead or left atrial lead) may also include at least one electrode capable of stimulating an autonomic nerve, non-myocardial tissue, other nerves, etc., wherein such an electrode may be positioned on the lead or a bifurcation or leg of the lead.

IMD 100 is also shown in electrical communication with the patient's heart 102 by way of an implantable right ventricular lead 108 having, in this exemplary implementation, a right ventricular tip electrode 128, a right ventricular ring electrode 130, a right ventricular (RV) coil electrode 132, and an SVC coil electrode 134. Typically, the right ventricular lead 108 is transvenously inserted into the heart 102 to place the right ventricular tip electrode 128 in the right ventricular apex so that the RV coil electrode 132 will be positioned in the right ventricle 113 and the SVC coil electrode 134 will be positioned in the superior vena cava. Accordingly, the right ventricular lead 108 is capable of sensing or receiving cardiac signals, and delivering stimulation in the form of pacing and shock therapy to the right ventricle. An exemplary right ventricular lead may also include at least one electrode capable of stimulating an autonomic nerve, non-myocardial tissue, other nerves, etc., wherein such an electrode may be positioned on the lead or a bifurcation or leg of the lead.

Figure 2:
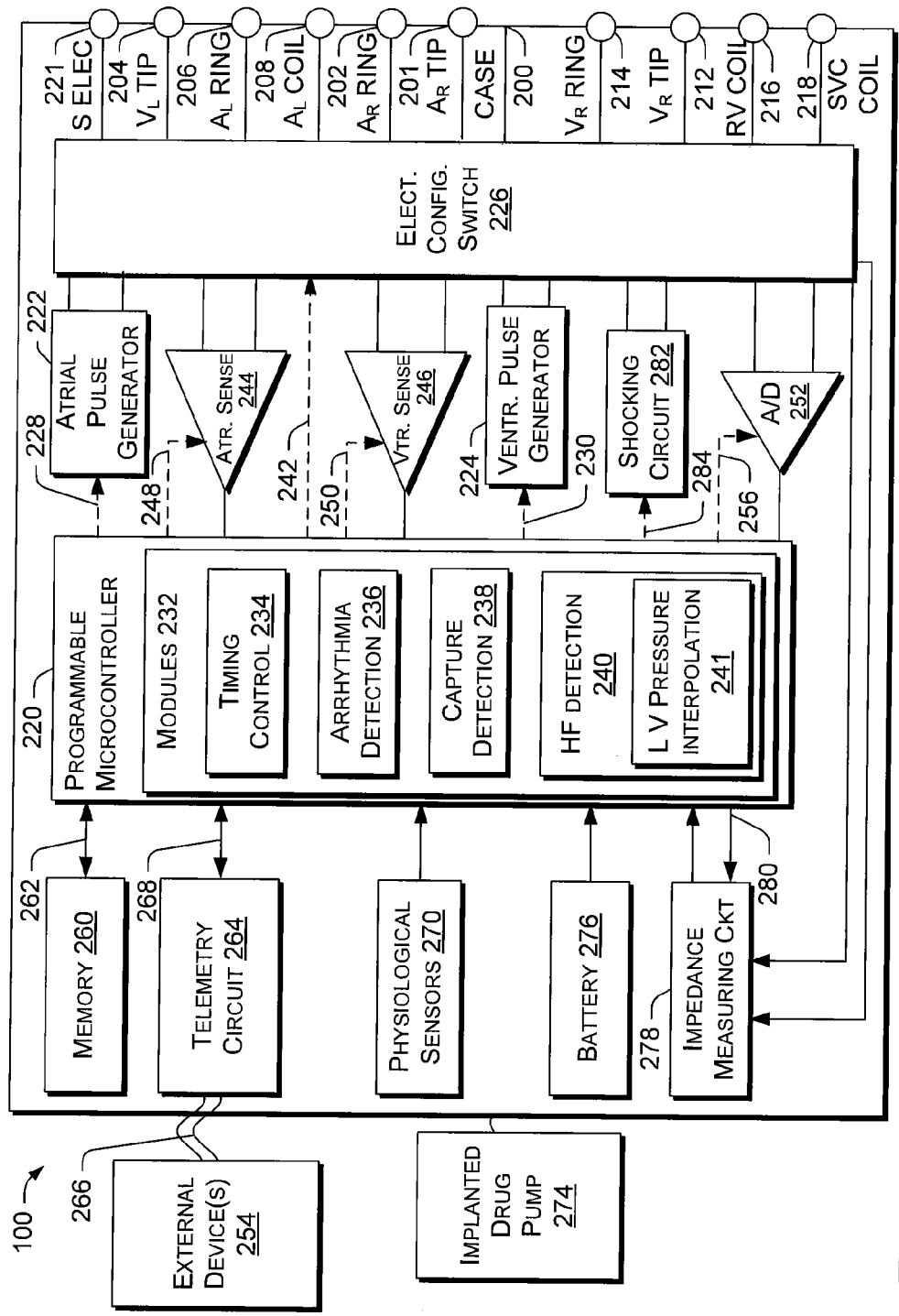
FIG. 2 is a functional block diagram of an exemplary implantable medical device (IMD) illustrating basic elements that are operable to interpolate left ventricular pressure in accordance with one implementation.

FIG. 2 shows an exemplary, simplified block diagram depicting various components of IMD 100. The IMD 100 can be capable of treating both fast and slow arrhythmias with stimulation therapy, including cardioversion, defibrillation, and pacing stimulation. The IMD can be solely or further capable of delivering stimuli to autonomic nerves, non-myocardial tissue, other nerves, etc. While a particular multi-chamber device is shown, it is to be appreciated and understood that this is done for illustration purposes only. Thus, the techniques and methods described below can be implemented in connection with any suitably configured or configurable IMD. Accordingly, one of skill in the art could readily duplicate, eliminate, or disable the appropriate circuitry in any desired combination to provide a device capable of treating the appropriate chamber(s) or regions of a patient's heart with cardioversion, defibrillation, pacing stimulation, autonomic nerve stimulation, non-myocardial tissue stimulation, other nerve stimulation, etc.

Housing 200 for IMD 100 is often referred to as the "can", "case" or "case electrode", and may be programmably selected to act as the return electrode for all "unipolar" modes. Housing 200 may further be used as a return electrode alone or in combination with one or more of the coil electrodes 125, 132 and 134 for shocking purposes. Housing 200 further includes a connector (not shown) having a plurality of terminals 201, 202, 204, 206, 208, 212, 214, 216, 218, 221 (shown schematically and, for convenience, the names of the electrodes to which they are connected are shown next to the terminals).

To achieve right atrial sensing and/or pacing, the connector includes at least a right atrial tip terminal ($A_R$ TIP) 201 adapted for connection to the atrial tip electrode 120. A right atrial ring terminal ($A_R$ RING) 202 is also shown, which is adapted for connection to the atrial ring electrode 121. To achieve left chamber sensing, pacing and/or shocking, the connector includes at least a left ventricular tip terminal ($V_L$ TIP) 204, a left atrial ring terminal ($A_L$ RING) 206, and a left atrial shocking terminal ($A_L$ COIL) 208, which are adapted for connection to the left ventricular tip electrode 122, the left atrial ring electrode 124, and the left atrial coil electrode 125, respectively. Connection to suitable autonomic nerve stimulation electrodes or other tissue stimulation or sensing electrodes is also possible via these and/or other terminals (e.g., via a nerve and/or tissue stimulation and/or sensing terminal S ELEC 221).

To support right chamber sensing, pacing, and/or shocking, the connector further includes a right ventricular tip terminal ($V_R$ TIP) 212, a right ventricular ring terminal ($V_R$ RING) 214, a right ventricular shocking terminal (RV COIL) 216, and a superior vena cava shocking terminal (SVC COIL) 218, which are adapted for connection to the right ventricular tip electrode 128, right ventricular ring electrode 130, the RV coil electrode 132, and the SVC coil electrode 134, respectively. Connection to suitable autonomic nerve stimulation electrodes or other tissue stimulation or sensing electrodes is also possible via these and/or other terminals (e.g., via a nerve and/or tissue stimulation and/or sensing terminal S ELEC 221).

At the core of the IMD 100 is a programmable microcontroller 220 that controls the various modes of stimulation therapy. As is well known in the art, microcontroller 220 typically includes a microprocessor, or equivalent control circuitry, designed specifically for controlling the delivery of stimulation therapy, and may further include RAM or ROM memory, logic and timing circuitry, state machine circuitry, and I/O circuitry. Typically, microcontroller 220 includes the ability to process or monitor input signals (data or information) as controlled by a program code stored in a designated block of memory. The type of microcontroller is not critical to the described implementations. Rather, any suitable microcontroller(s) 220 may be used that carries out the functions described herein. The use of microprocessor-based control circuits for performing timing and data analysis functions are well known in the art.

FIG. 2 also shows an atrial pulse generator 222 and a ventricular pulse generator 224 that generate pacing stimulation pulses for delivery by the right atrial lead 104, the coronary sinus lead 106, and/or the right ventricular lead 108 via an electrode configuration switch 226. It is understood that in order to provide stimulation therapy in each of the four chambers of the heart the atrial and ventricular pulse generators, 222 and 224, may include dedicated, independent pulse generators, multiplexed pulse generators, or shared pulse generators. The pulse generators 222 and 224 are controlled by the microcontroller 220 via appropriate control signals 228 and 230, respectively, to trigger or inhibit the stimulation pulses.

Microcontroller 220 further includes a plurality of modules 232 that, when executed, perform various functions of the IMD. For instance, the modules can perform arrhythmia detection, timing control, and/or morphology detection, among other functionalities.

The illustrated example specifically designates a timing control module 234, an arrhythmia detection module 236, a capture detection module 238, and a heart failure detection module 240.

Timing control module 234 controls the timing of the stimulation pulses (e.g., pacing rate, atrio-ventricular (AV) delay, atrial interconduction (A-A) delay, or ventricular interconduction (VV) delay, etc.) as well as to keep track of the timing of refractory periods, blanking intervals, noise detection windows, evoked response windows, alert intervals, marker channel timing, etc., which is well known in the art.

The arrhythmia detection module 236 and the capture detection module 238 can be utilized by the IMD 100 for detecting patient conditions and determining desirable times to administer various therapies such as pacing, defibrillation and/or in vivo dispensing of pharmaceuticals.

The heart failure detection module 240 provides a mechanism for ascertaining cardiac health or conversely heart failure. The heart failure detection module utilizes data collected by the IMD 100 and/or by other devices that may be internal or external to the patient to detect heart failure. The collected data can include data relating to blood pressures upstream and/or downstream of the left ventricle and data relating to cardiac valve events. Examples of mechanisms for sensing blood pressures and cardiac valve events are described in more detail below. Once detected, the heart failure detection module can cause an appropriate patient therapy to be administered such as via shocking and/or pacing therapy and/or by dispensing a drug(s).

In some configurations, the heart failure detection module 240 can employ a left ventricle pressure interpolation module 241 to derive information relating to the functionality of the left ventricle. As mentioned above, left ventricle functionality is a valuable indicator of heart failure that can be analyzed by the heart failure detection module. The left ventricle pressure interpolation module 241 can utilize blood pressure information sensed from upstream and/or downstream from the left ventricle and in some configurations cardiac valve events relating to the mitral and aortic valves to interpolate pressures of the left ventricle during a cardiac cycle. In essence, the left ventricle pressure interpolation module 241 approximates left ventricular pressures without directly sensing pressures within the left ventricle. Examples of techniques that can be employed by the left ventricle pressure interpolation module 241 are described below in relation to FIGS. 3-5.

The electronic configuration switch 226 includes a plurality of switches for connecting the desired electrodes to the appropriate I/O circuits, thereby providing complete electrode programmability. Accordingly, switch 226, in response to a control signal 242 from the microcontroller 220, determines the polarity of the stimulation pulses (e.g., unipolar, bipolar, combipolar, etc.) by selectively closing the appropriate combination of switches (not shown) as is known in the art.

Atrial sensing circuits 244 and ventricular sensing circuits 246 may also be selectively coupled to the right atrial lead 104, coronary sinus lead 106, and the right ventricular lead 108, through the switch 226 for detecting the presence of cardiac activity in each of the four chambers of the heart. Accordingly, the atrial (ATR. SENSE) and ventricular (VTR. SENSE) sensing circuits, 244 and 246, may include dedicated sense amplifiers, multiplexed amplifiers, or shared amplifiers. Switch 226 determines the "sensing polarity" of the cardiac signal by selectively closing the appropriate switches, as is also known in the art. In this way, the clinician may program the sensing polarity independent of the stimulation polarity. The sensing circuits (e.g., 244 and 246) are optionally capable of obtaining information indicative of tissue capture.

Each sensing circuit 244 and 246 preferably employs one or more low power, precision amplifiers with programmable gain and/or automatic gain control, bandpass filtering, and a threshold detection circuit, as known in the art, to selectively sense the cardiac signal of interest. The automatic gain control enables the IMD 100 to deal effectively with the difficult problem of sensing the low amplitude signal characteristics of atrial or ventricular fibrillation.

The outputs of the atrial and ventricular sensing circuits 244 and 246 are connected to the microcontroller 220, which, in turn, is able to trigger or inhibit the atrial and ventricular pulse generators 222 and 224, respectively, in a demand fashion in response to the absence or presence of cardiac activity in the appropriate chambers of the heart. Furthermore, as described herein, the microcontroller 220 is also capable of analyzing information output from the sensing circuits 244 and 246 and/or the data acquisition system 252 to determine or detect whether capture has occurred and to program a pulse, or pulses, in response to such determinations. The sensing circuits 244 and 246, in turn, receive control signals over signal lines 248 and 250 from the microcontroller 220 for purposes of controlling the gain, threshold, polarization charge removal circuitry (not shown), and the timing of any blocking circuitry (not shown) coupled to the inputs of the sensing circuits, 244 and 246, as is known in the art.

For arrhythmia detection, IMD 100 utilizes the atrial and ventricular sensing circuits, 244 and 246, to sense cardiac signals to determine whether a rhythm is physiologic or pathologic. In reference to arrhythmias, as used herein, "sensing" is reserved for the noting of an electrical signal or obtaining data (information), and "detection" is the processing (analysis) of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the arrhythmia detector 236 of the microcontroller 220 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to inputs of an analog-to-digital (A/D) data acquisition system 252. The data acquisition system 252 is configured to acquire intracardiac electrogram signals, convert the raw analog data into a digital signal, and store the digital signals for later processing and/or telemetric transmission to an external device(s) 254. The data acquisition system 252 is coupled to the right atrial lead 104, the coronary sinus lead 106, the right ventricular lead 108 and/or the nerve or other tissue stimulation lead 110 through the switch 226 to sample cardiac signals across any pair of desired electrodes.

External device 254 can be manifested as a programmer or device manager, among others. In other configurations, external device 254 can be one or more devices to sense arterial blood pressures and/or to detect audible heart sounds. In some cases, external device 254, such as in the form factor of a device manager that is carried with or otherwise kept proximate the patient can be multifunctional. The external device is multifunctional in that in can receive sensed data from the IMD and can also relay data from other external devices relating to sensed heart sounds and/or arterial pressures to the IMD 100 such as for use by the left ventricle pressure interpolation module 241.

The microcontroller 220 is further coupled to a memory 260 by a suitable data/address bus 262, wherein the programmable operating parameters used by the microcontroller 220 are stored and modified, as required, in order to customize the operation of the IMD 100 to suit the needs of a particular patient. Such operating parameters define, for example, pacing pulse amplitude, pulse duration, electrode polarity, rate, sensitivity, automatic features, arrhythmia detection criteria, and the amplitude, waveshape, number of pulses, and vector of each shocking pulse to be delivered to the patient's heart 102 within each respective tier of therapy.

Advantageously, the operating parameters of the IMD 100 may be non-invasively programmed into the memory 260 through a telemetry circuit 264 in telemetric communication via communication link 266 with the external device 254, such as a programmer, transtelephonic transceiver, or a diagnostic system analyzer. The microcontroller 220 activates the telemetry circuit 264 with a control signal 268. The telemetry circuit 264 advantageously allows intracardiac electrograms and status information relating to the operation of the device 100 (as contained in the microcontroller 220 or memory 260) to be sent to the external device 254 through an established communication link 266.

The IMD 100 can further include a physiologic sensor(s) 270 to detect one or more of patient activity, patient posture, and respirations, blood pressures, and cardiac events associated with opening and/or closing of heart valves, among others. Microcontroller 220 can utilize data received from the physiologic sensor(s) 270 to adjust the various pacing parameters (such as rate, AV Delay, VV Delay, etc.) at which the atrial and ventricular pulse generators, 222 and 224, generate stimulation pulses. Microcontroller 220 further can utilize data received from the physiologic sensor(s) 270 to identify heart failure via heart failure detection module 240.

While shown as being included within the IMD 100, it is to be understood that the physiologic sensor 270 may also be external to the IMD 100, yet still be implanted within or carried by the patient. Examples of physiologic sensors that may be implemented in IMD 100 include known sensors that, for example, sense pressure, respiration rate, pH of blood, cardiac output, preload, afterload, contractility, oxygen levels, audible cardiac events, and so forth. Another sensor that may be used is one that detects activity variance, where an activity sensor is monitored to detect the low variance in the measurement corresponding to the sleep state and/or maintenance of a specific posture.

The physiological sensors 270 optionally include sensors for detecting movement and minute ventilation in the patient. The physiological sensors 270 may include a position sensor and/or a minute ventilation (MV) sensor to sense minute ventilation, which is defined as the total volume of air that moves in and out of a patient's lungs in a minute. Signals generated by the position sensor and MV sensor are passed to the microcontroller 220 for analysis in determining whether to adjust the pacing rate, etc. The microcontroller 220 monitors the signals for indications of the patient's posture and activity status, such as whether the patient is climbing upstairs or descending downstairs or whether the patient is sitting up after supine down.

The IMD 100 optionally includes circuitry capable of sensing heart sounds and/or vibration associated with events that produce heart sounds. Heart sounds can be detected with any type of microphone or pressure sensing device such as accelerometer that can detect a pressure wave associated with opening or closing of a heart valve. Accelerometers as conventionally used for patient position and/or activity determinations can be utilized for detecting heart sounds by selecting a suitable band pass filter. Accelerometers typically include two or three sensors aligned along orthogonal axes. For example, a commercially available micro-electromechanical system (MEMS) marketed as the ADXL202 by Analog Devices, Inc. (Norwood, Mass.) has a mass of about 5 grams and a 14 lead CERPAK (approx. 10 mm by 10 mm by 5 mm or a volume of approx. 500 mm$^3$). The ADXL202 MEMS is a dual-axis accelerometer on a single monolithic integrated circuit and includes polysilicon springs that provide a resistance against acceleration forces. The term MEMS has been defined generally as a system or device having micro-circuitry on a tiny silicon chip into which some mechanical device such as a mirror or a sensor has been manufactured.

The aforementioned ADXL202 MEMS includes micro-circuitry and a mechanical oscillator.

While an accelerometer may be included in the case of an IMD in the form of an implantable pulse generator device, alternatively, an accelerometer communicates with such a device via a lead or through electrical signals conducted by body tissue and/or fluid. In the latter instance, the accelerometer may be positioned to advantageously sense vibrations associated with cardiac events. For example, an epicardial accelerometer may have improved signal to noise for cardiac events compared to an accelerometer housed in a case of an implanted pulse generator device.

IMD 100 may also include, or be in communication with, an implanted drug pump 274 or other drug delivery mechanism to effect patient therapy. The drug pump can be activated in various scenarios, such as when a heart failure condition is detected by heart failure detection module 240.

The IMD 100 additionally includes a battery 276 that provides operating power to all of the circuits shown in FIG. 2. For the IMD 100, which employs shocking therapy, the battery 276 is capable of operating at low current drains for long periods of time (e.g., preferably less than 10 μA), and is capable of providing high-current pulses (for capacitor charging) when the patient requires a shock pulse (e.g., preferably, in excess of 2 A, at voltages above 200 V, for periods of 10 seconds or more). The battery 276 also desirably has a predictable discharge characteristic so that elective replacement time can be detected.

The IMD 100 can further include magnet detection circuitry (not shown), coupled to the microcontroller 220, to detect when a magnet is placed over the IMD 100. A magnet may be used by a clinician to perform various test functions of the IMD 100 and/or to signal the microcontroller 220 that the external programmer 254 is in place to receive or transmit data to the microcontroller 220 through the telemetry circuits 264. Trigger IEGM storage also can be achieved by the magnet.

The IMD 100 further includes an impedance measuring circuit 278 that is enabled by the microcontroller 220 via a control signal 280. The known uses for an impedance measuring circuit 278 include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance, such as for determining shock thresholds, (HF indications—pulmonary edema and other factors); detecting when the device has been implanted; measuring stroke volume; and detecting the opening of heart valves, etc. The impedance measuring circuit 278 is advantageously coupled to the switch 226 so that any desired electrode may be used.

In the case where the IMD 100 is intended to operate as an implantable cardioverter/defibrillator (ICD) device, it detects the occurrence of an arrhythmia, and automatically applies an appropriate therapy to the heart aimed at terminating the detected arrhythmia. To this end, the microcontroller 220 further controls a shocking circuit 282 by way of a control signal 284. The shocking circuit 282 generates shocking pulses in a range of joules, for example, conventionally up to about 40 J, as controlled by the microcontroller 220. Such shocking pulses are applied to the patient's heart 102 through at least two shocking electrodes, and as shown in this embodiment, selected from the left atrial coil electrode 125, the RV coil electrode 132, and/or the SVC coil electrode 134. As noted above, the housing 200 may act as an active electrode in combination with the RV electrode 132, or as part of a split electrical vector using the SVC coil electrode 134 or the left atrial coil electrode 125 (i.e., using the RV electrode as a common electrode).

Cardioversion level shocks are generally considered to be of low to moderate energy level (so as to minimize battery drain and the more rapid delivery of the shock if the lower energy levels are effective in restoring a normal rhythm), and/or synchronized with an R-wave and/or pertaining to the treatment of tachycardia. Defibrillation shocks are generally of moderate to high energy level (i.e., corresponding to thresholds in the range of approximately 5 J to approximately 40 J), delivered asynchronously (since R-waves may be too disorganized), and pertaining exclusively to the treatment of fibrillation. Accordingly, the microcontroller 220 is capable of controlling the synchronous or asynchronous delivery of the shocking pulses.

In low-energy cardioversion, an IMD typically delivers a cardioversion stimulus (e.g., 0.1-5 J, etc.) synchronously with a QRS complex; thus, avoiding the vulnerable period of the T wave and avoiding an increased risk of initiation of VF. In general, if antitachycardia pacing or cardioversion fails to terminate a tachycardia, then, for example, after a programmed time interval or if the tachycardia accelerates, the IMD initiates defibrillation therapy.

While an IMD may reserve defibrillation as a latter tier therapy, it may use defibrillation as a first-tier therapy for VF. In general, an IMD does not synchronize defibrillation therapy with any given portion of a ECG. Again, defibrillation therapy typically involves high-energy shocks (e.g., 5 J to 40 J), which can include monophasic or unidirectional and/or biphasic or bidirectional shock waveforms. Defibrillation may also include delivery of pulses over two current pathways.

Exemplary Left Ventricular Interpolation Techniques

Figure 3:
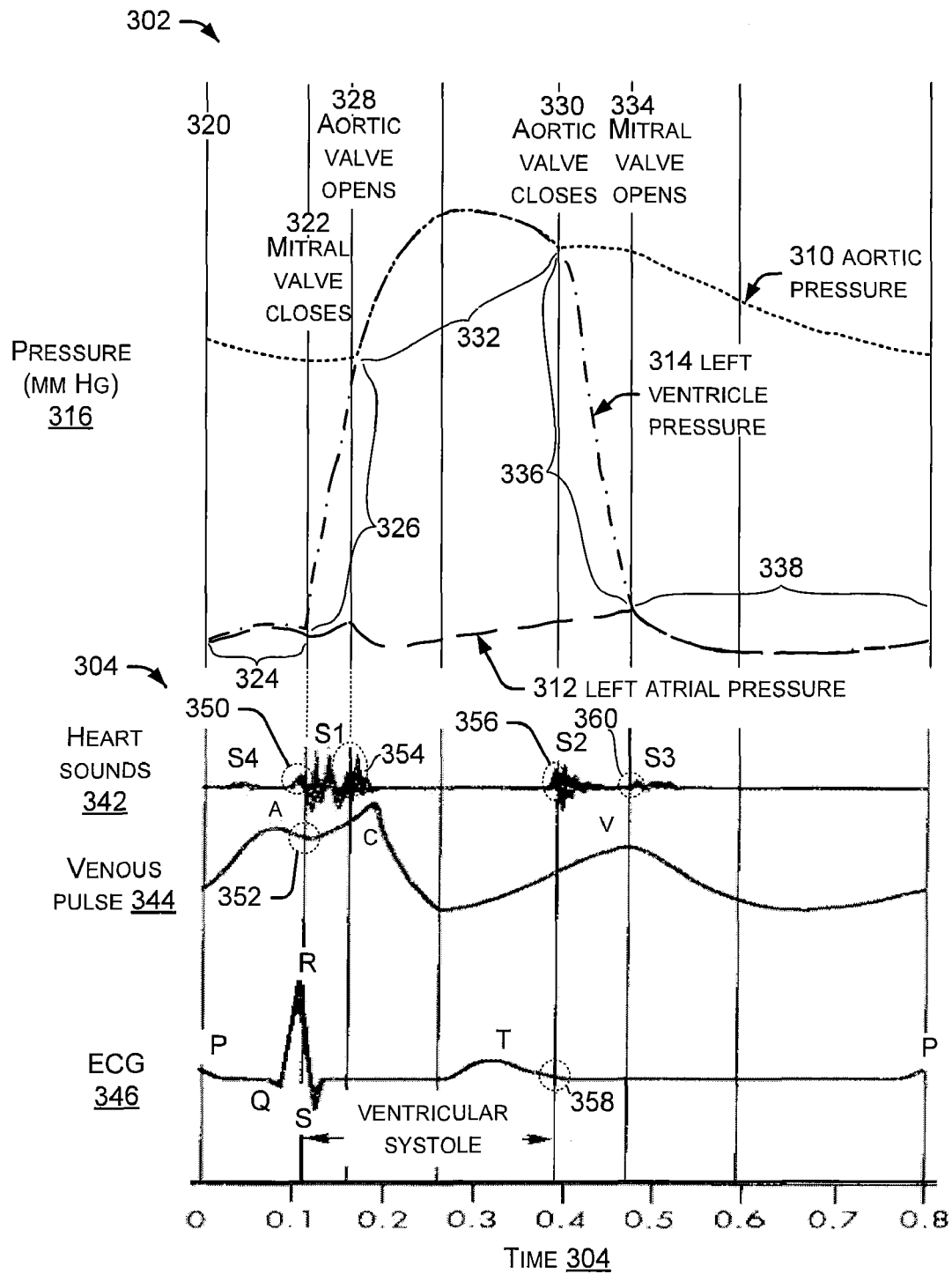
FIG. 3 is a plot of various cardiac related pressures and cardiac data that can be utilized to interpolate left ventricular pressure in accordance with various implementations.

FIG. 3 illustrates concurrent plots 302, 304 of several different parameter values over time. The described inventive concepts allow determination of left ventricular pressures without directly sensing blood pressure in the left ventricle. Instead, the inventive concepts interpolate left ventricular pressure data from other available cardiac related data. Plot 302 represents sensed blood pressure parameters from which left ventricular pressures can be interpolated, while plot 304 represents examples of three parameters that can be utilized to detect cardiac valve events. Both plots are illustrated in relation to time 310 along the horizontal or x-axis where the duration of time 310 represents one cardiac cycle lasting approximately 0.8 seconds.

Plot 302 represents aortic pressure as dotted line 310, left atrial pressure as dashed line 312, and left ventricular pressure as line 314 (alternating dashes and dots). Pressure values for the aortic, left atrial, and left ventricle pressures are represented vertically along the y-axis as pressure in millimeter of mercury (mm HG) 316.

Aortic pressure can be sensed utilizing various sensing mechanisms. Further, aortic pressure can be sensed directly or indirectly via an artery. In one scenario, aortic pressure can be sensed directly by a sensor extended across the atrial septum into the root of the aorta. Another sensing mechanism is manifest as a tonometer that is positioned on or around the aorta. Other scenarios involve sensing arterial pressures and approximating aortic pressures from the arterial pressures. Arterial pressures offer a reasonable surrogate of aortic pressures and the skilled artisan can compensate for any difference between the arterial pressure and the aortic pressure such as may be caused by the elastic nature of the arteries. Internal or external sensing mechanisms can be employed for sensing arterial pressure. For instance, arterial pressure can be sensed with a traditional pressure cuff positioned around the patient's arm to sense pressure in the brachial artery. Other mechanisms such as a tonometer can be employed invasively to sense arterial pressure.

Left atrial pressure 312 can be sensed utilizing various sensing mechanisms. In one scenario, a sensing mechanism is extended from the right atrium through the atrial septum into the left atrium to sense left atrial pressures.

For purposes of explanation, assume that in a first scenario both aortic pressure 310 and left atrial pressure 312 are sensed or otherwise obtained for the duration of time 304. Starting arbitrarily at the left-most portion 320 of plot 302 assume that the patient's mitral valve is open and the aortic valve is closed. At this point in the cardiac cycle, the left atrium is contracting and the left ventricle is relaxed. During these conditions, blood is flowing freely from the left atrium into the left ventricle. Subsequently, the left ventricle begins to contract, and at about the same time, the mitral valve closes as indicated at 322. When looking specifically at left atrial pressure 312, hemodynamics indicates that for a period 324 defined between point 320 and mitral valve closing 322 that blood pressures within the left atrium and the left ventricle are approximately equal. Accordingly, for period 324 the left ventricular pressure 314 can be interpolated from the left atrial pressure 312.

Upon closure of the mitral valve at 322, the left atrium and left ventricle again form separate non-connected chambers and pressure within the left ventricle diverges from the pressure in the left atrium as the left ventricle contracts. Both the mitral valve leading into the left ventricle and the aortic valve leading out of the left ventricle are closed for a period 326 known as isovolumic contraction. The present concepts can interpolate the left ventricular pressures during period 326 as will be described below after the remainder of plot 302 is discussed.

Continuing with plot 302, at point 328 the aortic valve leading from the left ventricle into the aorta opens. With the opening of the aortic valve, blood flows from the left ventricle into the aorta and pressures within the left ventricle and the aorta generally equalize. Pressure within the left ventricle and the aorta remain generally equal until the aortic valve closes at point 330. Accordingly, for a period 332 extending between opening of the aortic valve at 328 and closing of the aortic valve at 330, the left ventricular pressure can be interpolated from the aortic pressure. Stated another way, during period 332 aortic pressure 310 offers a reasonable surrogate for left ventricular pressure 314.

The closing of the aortic valve at 330 causes the left ventricle to be fluidly separated from the aorta. Subsequently, as the left ventricle relaxes its volume expands resulting in decreasing pressures within the left ventricle until the mitral valve opens at 334. Opening of the mitral valve at 334 occurs as blood is pumped into the left ventricle from the left atrium. Left ventricular pressure during a period 336 defined between the closing of the aortic valve at 330 and the opening of the mitral valve at 334 can be interpolated as will be described below.

Continuing with plot 302, after the mitral opens at 334 blood flows into the left ventricle from the left atrium and the pressures within the left ventricle and the left atrium generally equalize for a period 338 extending between mitral valve opening 334 and the right side of the plot. The right side of the plot can, of course, be extended into the same point in the next cardiac cycle as is represented in the left side of the plot at point 320. For period 338 as with period 324, the left ventricular pressure can be interpolated from the left atrial pressure.

As mentioned above in periods 326, 336 the left ventricular pressure does not directly correlate with either of the left atrial pressure or the aortic pressure. However, the present implementations can interpolate the left ventricular pressure from one or both of the left atrial pressure and the aortic pressure. For instance, some of these techniques employ curve fitting to obtain an approximation of the corresponding left ventricular pressures. In one example, the available pressure data from period 332 can be utilized with curve fitting to interpolate the pressures of either or both of periods 326 and 336. Similarly, pressure data from period 324 can be utilized to interpolate pressures in period 326 and pressure data in period 338 can be utilized to interpolate pressures in period 336. In the present example where both left atrial pressures and aortic pressures are available, both the left atrial and aortic pressures can be utilized in the interpolation process. In other scenarios only one of the left atrial or aortic pressures may be available from which to interpolate the left ventricular pressure. Still other implementations can interpolate the left ventricular pressures from one or both of the left atrial pressure and the aortic pressure in combination with sensed or detected cardiac valve events.

Plot 304 provides several examples for detecting cardiac valve events related to the mitral and aortic valves. Three parameters 342, 344, and 346 are represented in plot 304 that can be utilized to detect some or all of the cardiac valve events of interest. Parameter 342 relates to heart sound data, parameter 344 relates to venous pulse data and parameter 346 relates to electrocardiogram (ECG) data.

Figure 4:
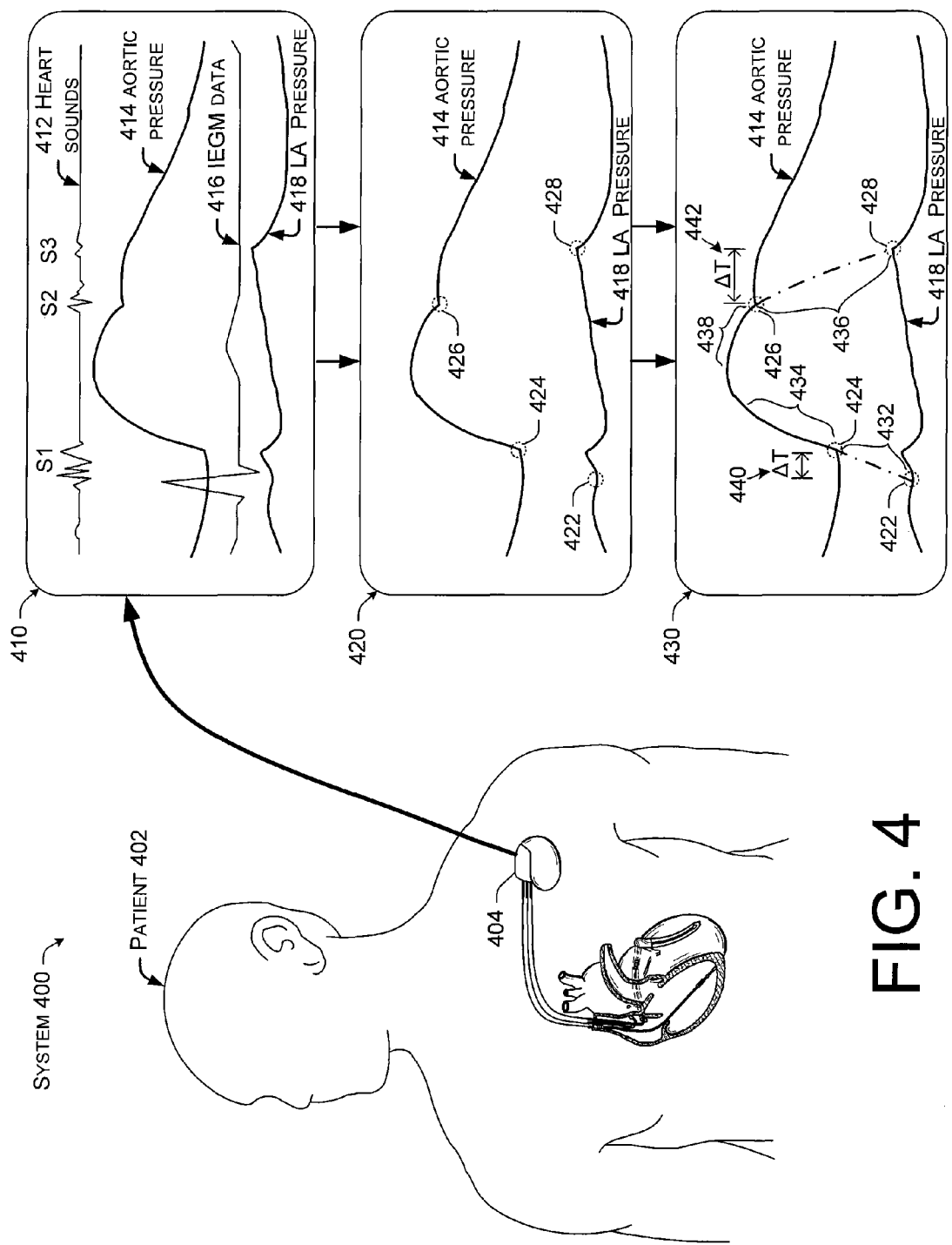
FIGS. 4-5 are systems that can interpolate left ventricular pressure in accordance with various implementations.
Figure 5:
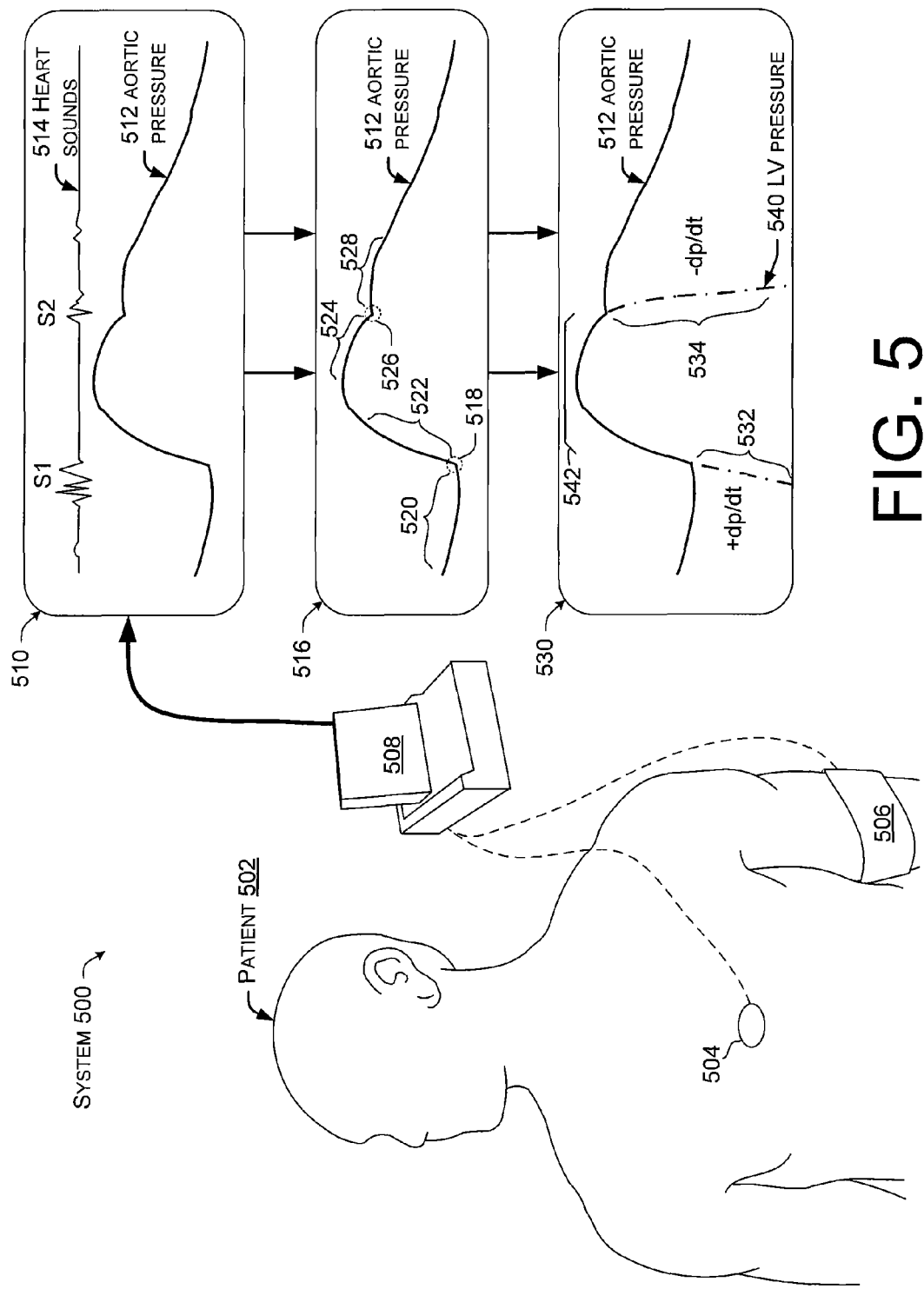

Heart sound parameter 342 includes 4 distinct heart sounds indicated as S1, S2, S3, and S4. (Due to the arbitrary starting point of plots 302, 304 in the cardiac cycle, heart sound S4 occurs first in time in plot 304 (i.e., farthest to the left)). Heart sounds can be detected with various types of detection mechanisms. For instance, heart sounds can be sampled with accelerometers, microphones, and or pressure transducers, among others. The heart sound detection mechanisms can be positioned external to a patient or internally. FIGS. 2 and 4 provide an example where the heart sound detection mechanism is positioned internally the patient, such as within the housing of an IMD. In another case, the heart sound detection mechanism can be positioned upon a lead that is positioned in the patient's vasculature or heart. FIG. 5 provides an example where the heart sound detection mechanism is positioned externally. The skilled artisan should recognize other configurations that are consistent with the concepts described above and below.

Venous pulse parameter 344 includes three labeled regions including an "A" peak, a "C" peak, and a "V" peak. Venous pulse pressure can be detected utilizing various mechanisms. For example, venous pulse pressures can be detected with a pressure sensing mechanism positioned in the right atrium. Other venous pulse pressure sensing mechanisms can be positioned directly on or in the venous vasculature.

Electrogram parameter 346 includes peaks or waves labeled as "P", "Q", "R", "S", and "T". Electrogram data can be detected with various mechanisms. One such mechanism is described in detail above in relation to FIGS. 1-2 for sensing internal electrogram data. Other mechanisms can sense electrogram data externally via one or more sensors positioned upon the patient's skin proximate the thorax.

Mitral valve closure (322) can be detected from any of parameters 342, 344, and 346. For instance, in relation to heart sound parameter 342 mitral valve closure corresponds to the S1 heart sound generally. Specifically, a first positive peak 350 of the S1 heart sound generally corresponds to mitral valve closure as evidenced along the vertical axis. In relation to venous pulse parameter 344, mitral valve closure generally corresponds to a negative peak value 352 occurring between positive peak A and positive peak C. In relation to electrogram parameter 346 mitral valve closure corresponds to the R peak of the QRS complex.

Aortic valve opening (328) can be detected from the heart sound parameter 342 as a last peak 354 of heart sound S1. Aortic valve closing (330) can be detected utilizing heart sound parameter 342 specifically as a first peak 356 of heart sound S2. The aortic valve opening can also be detected from the ECG parameter by the culmination of the T-wave as indicated at 358. Mitral valve opening can be detected from the heart sound parameter 342 by the first peak 360 of the S3 heart sound. The skilled artisan should recognize other techniques or combinations of techniques for detecting one or more of mitral valve opening, mitral valve closure, aortic valve opening and/or aortic valve closure. The above description relating to FIG. 3 generally introduces techniques for interpolating left ventricular pressures from other available cardiac related data. FIGS. 4-5 provide specific examples for interpolating the left ventricular pressure data. Stated another way, the description related to FIGS. 4-5 offers techniques for indirectly determining left ventricular pressures without directly sensing the left ventricle.

First Exemplary Left Ventricular Interpolation System

FIG. 4 illustrates a system 400 for interpolating left ventricular pressure data from cardiac related data detected internally from a patient 402. In this case, an IMD 404, similar to the IMD described above in relation to FIGS. 1-2, senses the cardiac related data and interpolates left ventricular pressure data from the sensed cardiac related data. The IMD 404 can then utilize the interpolated left ventricular pressure data to ascertain a patient condition and/or in formulating an appropriate patient therapy.

In this instance, as indicated generally at plot 410, IMD 404 senses cardiac related data in the form of heart sounds 412, aortic pressure 414, intracardiac electrogram (IEGM) data 416, and left atrial pressure 418. Utilizing the heart sounds 412 and/or IEGM data 416, the IMD can determine points where the left ventricular pressure diverges from, and converges with, the left atrial pressure 418 and the aortic pressure 414. For instance, as indicated generally at plot 420, left ventricular pressure diverges from left atrial pressure 418 at point 422. As discussed above in relation to FIG. 3, point 422 corresponds to the peak of the IEGM's R-wave and to the initial portions or peak of the S1 heart sounds. Left ventricular pressure converges with aortic pressure 414 at a point 424 that corresponds to the culmination of the S1 heart sound. Similarly, divergence of the left ventricular pressure from the aortic pressure 414 occurs at point 426 that corresponds to heart sound S2. Finally, convergence of the left ventricular pressure with the left atrial pressure 418 occurs at a point 428 that corresponds to the S3 heart sound. In summary, starting at the left-most portion of plot 420 and continuing until point 422, the left ventricular pressure can effectively be considered to be equal to the left atrial pressure 418. From point 424 to point 426, the left atrial pressure can effectively be considered to be equal to the aortic pressure 414. Subsequent to point 428 the left ventricular pressure can once again be considered to be equal to the left atrial pressure 418.

As indicated generally at 430, the IMD can interpolate remaining unknown left ventricular pressures. For instance, the IMD can employ curve fitting to interpolate the remaining left ventricular pressure values. In this case, left ventricular pressure 432 can be interpolated between points 422 and 424 at least in part by curve fitting from region 434 where the left ventricular pressure are generally equivalent to the aortic pressures 414. In a similar manner, ventricular pressure 436 can be interpolated between points 426 and 428 at least in part by curve fitting from known pressure region 438 where the left ventricular pressure are generally equivalent to the aortic pressures 414.

The IMD can ascertain various parameter values from the interpolated left ventricular pressure data to ascertain a patient condition. For instance, one parameter that can be utilized for ascertaining a patient condition is left ventricular end diastolic pressure (LVEDP) which is a measure of preload of the left ventricle. LVEDP can indicate how well the heart is functioning, or conversely, a high or rising LVEDP value can indicate that the heart is falling behind in its pumping function resulting in increased preload. Point 422 represents divergence of left atrial and left ventricular pressures associated with the end of LVEDP and the beginning of left ventricular systole. As mentioned above, left ventricular pressures are generally equivalent to left atrial pressures prior to point 422. Accordingly, the present implementations can ascertain LVEDP parameter values as the left atrial pressure at (or directly preceding) point 422. Thus, the present implementations can ascertain LVEDP values from left atrial pressure values at point 422 or at a slightly preceding point. For example, left atrial pressure values from a point that is, for instance, 10-20 milliseconds before point 422, may be slightly more accurate than a left atrial value measured exactly at point 422. The 10-20 millisecond range is provided for purposes of example and is not intended to be limiting. Other examples could ascertain the parameter values from more than about 100 milliseconds to about 1 millisecond before point 422. LVEDP offers but one example of parameters that can be determined utilizing the present techniques.

The present implementations can determine other parameter values related to left ventricular function. For instance, other parameter values relate to a duration of isovolumic contraction and a duration of isovolumic relaxation of the left ventricle. These parameter values can be determined from plot 430. For instance, a duration of isovolumic contraction can be determined as a change in time ($\Delta T$) indicated at 440 from mitral valve closing at 422 to aortic valve opening at 424. Similarly, a duration of isovolumic relaxation can be determined as a change in time ($\Delta T$) indicated at 442 from aortic valve closing at 426 to mitral valve opening at 428. FIG. 5 describes still other examples of left ventricular functionality that can be determined utilizing the present implementations.

One or more of the determined or interpolated left ventricular parameter values can be utilized by the IMD to diagnose a patient condition and/or to formulate a responsive patient therapy. In one scenario, the IMD may diagnose that the patient is experiencing heart failure based at least in part upon the determined parameter values. For instance, the determined LVEDP values may indicated that the heart is falling behind in its pumping function and that residual blood volume is rising. The IMD can then formulate a responsive patient therapy such as increasing a pacing rate and/or causing a drug to be delivered to the patient. The IMD may alternatively or additionally cause an alarm signal to be sent to an external device relating to the patient condition. Examples of mechanisms for increasing the pacing rate and drug delivery are described above in relation to FIGS. 1-2.

Second Exemplary Left Ventricular Interpolation System

FIG. 5 illustrates a system 500 for interpolating left ventricular pressure data from cardiac related data detected externally from a patient 502. In this case, a microphone 504 for detecting heart sounds is adhered to the skin of the patient's thorax. A pressure cuff 506 is positioned around the patient's arm to sense arterial pressure in the patient's brachial artery. Microphone 504 and pressure cuff 506 are electrically coupled to computing device 508. The computing device can be manifest in various form factors including, a device manager, a programmer, and a personal computing device, among others. As represented generally at plot 510, the computing device can receive the patient's pressure data (graphically represented at 512) and heart sounds (graphically represented at 514).

Computing device 508 can process the patient's pressure data 512 and/or heart sounds 514 to detect points where left ventricular pressure converges with and/or diverges from aortic pressure. In one such example, indicated generally at plot 516, computing device 508 can detect convergence of left ventricular pressure with aortic pressure 512 at a point 518 which marks a transition from generally declining aortic pressures of a curve 520 to generally increasing pressures of curve 522. Similarly, left ventricular pressure divergence from aortic pressure 512 associated with aortic valve closing can be detected as a sudden transition from a curve 524 at a point 526 to a different curve 528, where both curves 524, 528 have negative slopes but of differing values. The left ventricular pressure can be generally equivalent to the aortic pressure between points 518 and 526.

Alternatively or additionally, the convergence and divergence of the left ventricular pressure and aortic pressure can be detected from the heart sounds 514. For instance, the end of the S1 heart sound can indicate aortic valve opening associated with point 518, and the beginning of the S2 heart sound can be indicative of aortic valve closing associated with point 526.

As indicated generally at plot 530 in combination with plot 516, regardless of how left ventricular and aortic pressure convergence and divergence are determined, the computing device 508 can then utilize a technique such as curve fitting to interpolate additional left ventricular pressure data. For instance, curve fitting can be applied relative to curves 522, 524 to interpolate at least some of the ventricular pressures that are otherwise unavailable without direct sensing. In this case, curve fitting applied to curve 522 produces interpolated curve 532 and curve fitting applied to curve 524 produces interpolated curve 534. Interpolated curves 532, 534 approximate left ventricular pressure data without directly sensing in the left ventricle. Stated another way, the exemplary concepts allow left ventricular pressure 540 to be interpolated for curves 532 and 534. Further, for the intervening region 542 between points 518 and 526 the exemplary concepts interpolate the left ventricular pressure 540 from the aortic pressure 512.

Interpolated left ventricular pressure 540 can be analyzed to ascertain a patient condition. In one case, interpolated curves 532, 534 can be analyzed to determine a patient condition. For instance, two parameters of interest associated with left ventricular function relate to a change in pressure over a change in time (dp/dt). Ascending pressure (+dp/dt) can be measured from interpolated curve 532 and relates to isovolumic contraction of the left ventricle. Similarly, descending pressure (−dp/dt) can be measured from interpolated curve 534 and relates to relaxation and flexibility of the left ventricle. Knowledge regarding +dp/dt and/or −dp/dt can enhance patient diagnosis and the efficacy of any resulting patient therapy.

In the example of FIG. 5 patient data (i.e., heart sounds and aortic pressure data) is obtained non-invasively from the patient. Processing the data and interpolation of left ventricular pressure data is accomplished by an external device. Conversely, the example of FIG. 4 collects the patient data internally from the patient and data processing and interpolation occur internally on the IMD. Rather than being exclusively internal or external, other implementations can include both internal and external facets. For example, some implementations can employ an internal IMD in communication with an external computing device or devices. In these implementations, cardiac related data can be sensed internally, externally, and/or a combination thereof, with either or both of the IMD and the external computing devices involved in interpolating the left ventricular pressures, diagnosing a patient condition, and formulating a responsive patient therapy.

Operation

Figure 6:
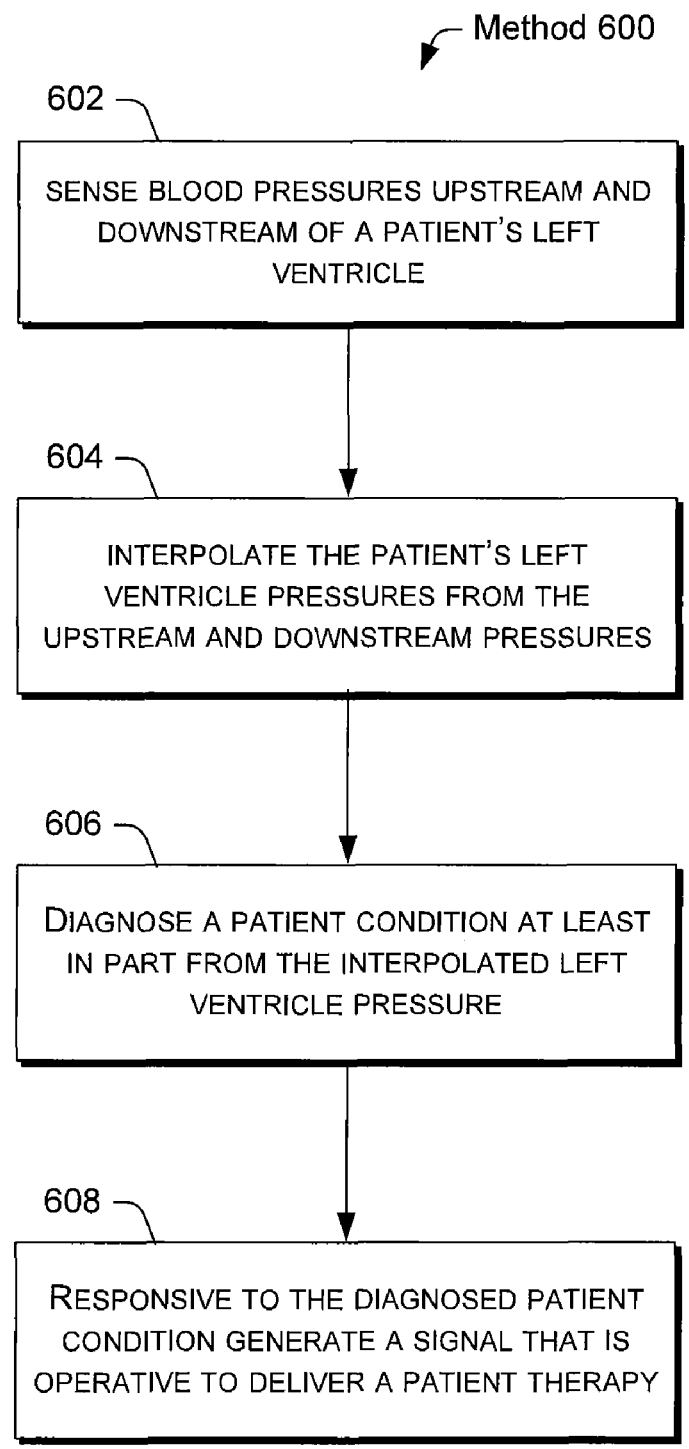
FIG. 6 is a flowchart of an exemplary method for interpolating left ventricular pressure in accordance with one implementation.

FIG. 6 shows an exemplary method or technique 600 for approximating left ventricular functionality. Method 600 offers an example for determining pressures within the left ventricle from blood pressures gathered without or outside the left ventricle. This method 600 may be implemented in connection with any suitably configured implantable medical devices (IMDs), external devices and/or systems. Non-limiting examples of devices and/or systems upon which the method can be implemented are described above in relation to FIGS. 1-5. Method 600 includes blocks 602-608. The order in which the method is described is not intended to be construed as a limitation, and any number of the described blocks can be combined in any order to implement the method, or an alternate method. Furthermore, the methods can be implemented in any suitable hardware, software, firmware, or combination thereof such that a computing device can implement the method. In one such instance, a computing device in the form of an implantable medical device (IMD), implements some or all of the method. In another instance, an external computing device such as a programmer, implements some or all of the method. In still another instance, one or more blocks are performed by an IMD and one or more blocks are performed by an external device. For example, a first block of the method can be performed by an IMD and then data can be transmitted to an external IMD for further processing consistent with other method blocks. In one case, the method is stored on a computer-readable media as a set of instructions such that execution by a computing device, such as an IMD, causes the computing device to perform the method.

At block 602, blood pressures upstream and downstream of a patient's left ventricle are sensed. Recognizing that the circulatory system is a closed system, the terms upstream and downstream are utilized in relation to blood flowing into and out of the left ventricle respectively. Accordingly, the left atrium is directly upstream of the left ventricle and the aorta is directly downstream.

In some implementations the upstream blood pressures are sensed from the left atrium and the downstream blood pressures are sensed from the aorta. In other instances the downstream pressures are sensed from one or more arteries supplied by the aorta. Non-limiting examples of invasive and non-invasive sensing mechanisms are described above in relation to FIGS. 1-5.

At block 604, the patient's left ventricular pressures are interpolated from the upstream and downstream pressures. The present concepts recognize instances where left ventricular blood pressure is approximately equal to one of left atrial pressure or aortic pressure. Some implementations can identify these instances by recognizing pressure changes caused by the left ventricle becoming hemodynamically connected to, or separated from, the left atrium and/or the aorta. For instance, opening of the aortic valve causes a sudden increase in aortic pressure as blood rushes from the left ventricle into the aorta. This sudden pressure increase in the aorta is distinct on the aortic pressure curve as evidenced in FIG. 3 and can be utilized to detect the aortic valve opening event. Stated another way, recognition of the sudden aortic pressure rise can provide a guidepost to convergence of left ventricular pressure and aortic pressure. Aortic valve opening can be determined as directly preceding the guidepost.

Other implementations determine when the left ventricle becomes hemodynamically connected to, or separate from, the left atrium and the aorta by correlating cardiac events with upstream and downstream pressure data. Stated another way, the cardiac events offer guideposts for when the left ventricle becomes hemodynamically connected to, or separated from, the left atrium and/or the aorta. For instance, the left ventricle becomes hemodynamically separated from the left atrium upon mitral valve closure. Mitral valve closure can be detected from heart sounds, cardiac electrogram data (either externally or internally sensed), and/or venous pressures, among others. Aortic valve opening can be similarly detected. The method can correlate the mitral valve closure and aortic valve opening to the left atrial and aortic pressures. The left ventricular pressure can be interpolated from the left atrial pressure for a period prior to mitral valve closure. The left ventricular pressure can also interpolated from the aortic pressure for a period following the aortic valve opening. The left ventricular pressure can be interpolated in the intervening period between mitral valve closure and aortic valve opening. In one instance, the left ventricular pressure in the intervening period is interpolated by curve fitting from the aortic pressure curve following aortic valve closure back through a point corresponding to aortic valve closure and toward a point on the left atrial pressure curve corresponding to mitral valve closure.

Similar interpolation techniques can be applied to obtain the left ventricular pressures between aortic valve closure and mitral valve opening. For example, aortic valve closure causes the left ventricle to be hemodynamically isolated from the aorta. Aortic valve closure can be detected from the heart sounds and IEGM data, among other techniques. Correspondingly, aortic valve closure can be correlated to a point on the aortic pressure to indicate where the left ventricular pressure diverges from the aortic pressure. Mitral valve opening again causes the left ventricle to be hemodynamically connected to the left atrium such that left ventricular pressure can once again be interpolated from left atrial pressure. Mitral valve opening can be detected from the S3 heart sounds, among other techniques. Thus, correlation of the S3 heart sounds with the left atrial pressure curve can identify the point of convergence between the left ventricular pressure and left atrial pressure. Curve fitting can be applied to the aortic pressures approaching and extending though the point of aortic valve closure and extending down to the point on the left atrial pressures corresponding to mitral valve opening.

At block 606, a patient condition can be diagnosed based, at least in part, upon the interpolated left ventricle pressures. For instance, the left ventricular pressures can be analyzed utilizing various known parameters (several examples of which are discussed above in relation to FIGS. 4-5). The parameter values obtained from the left ventricular data can be indicative of left ventricular functionality and ultimately of cardiac health or lack thereof (i.e., heart failure).

Responsive to the diagnosed patient condition a signal can be generated that is operative to deliver a patient therapy at 608. The signal can relate to various mechanisms for delivering patient therapy. For instance, the signal may relate to cardiac pacing as delivered by an IMD. In another case, the signal may cause a drug to be delivered to the patient. In still another case, the signal may cause a multifaceted patient therapy. For example, the signal may affect patient pacing and cause drug delivery to the patient. FIGS. 1-2 describe an IMD configured to accomplish such an implementation. In other instances, the signal may cause an IMD to deliver a first aspect of the patient therapy and another device to deliver a second aspect of the patient therapy. For instance, an IMD may receive the signal to deliver pacing therapy, while another device such as an external IV drug pump receives the signal to deliver drug therapy.

Conclusion

Exemplary techniques, methods, devices, systems, etc., relating to interpolating left ventricular pressures are described above. Interpolating left ventricular pressure allows the patient's cardiac condition to be diagnosed while obviating the need to directly sense left ventricular pressures. Although techniques, methods, devices, systems, etc., relating to interpolating left ventricular pressures are described above have been described in language specific to structural features and/or methodological acts, it is to be understood that the subject matter defined in the appended claims is not necessarily limited to the specific features or acts described. Rather, the specific features and acts are disclosed as exemplary forms of implementing the claimed methods, devices, systems, etc.

What is claimed is:

1. A system for interpolating left ventricle pressure in a patient comprising:
   a first sensor configured to monitor aortic pressure of the patient;
   a second sensor configured to monitor left atrial pressure of the patient;
   a third sensor configured to monitor cardiac valve events of the patient; and
   a processor programmed to interpolate left ventricle pressure of the patient based on a first point and a second point of a waveform corresponding to the monitored aortic pressure by the first sensor as a function of time, and a first point and a second point of a waveform corresponding to the monitored left atrial pressure by the second sensor as a function of time, wherein the first point of the measured left atrial pressure corresponds in time with a first of the monitored cardiac valve events by the third sensor and the second point of the measured left atrial pressure corresponds in time with a second of the monitored cardiac valve events by the third sensor;
   wherein the second point of the monitored aortic pressure coincides with a sudden transition from declining aortic pressures of a first negative slope to declining aortic pressures of a second negative slope less than the first negative slope.

2. The system of claim 1, wherein the first sensor is adapted to be positioned proximate to the aorta of the patient.

3. The system of claim 1, wherein the first sensor is configured to sense arterial pressure and the processor is programmed to approximate the aortic pressure from the sensed arterial pressure.

4. The system of claim 1, wherein the second sensor comprises a pressure sensor adapted to be positioned in the left atrium of the patient.

5. The system of claim 1, wherein the third sensor comprises a pair of electrodes configured to sense intracardiac electrograms (IEGM) and the processor is programmed to detect cardiac valve events from the IEGM.

6. The system of claim 1, wherein the third sensor comprises a sensor adapted to sense heart sounds and the processor is programmed to detect cardiac valve events from the heart sounds.

7. The system of claim 1, wherein the processor is programmed to employ curve fitting to interpolate the left ventricle pressure.

8. The system of claim 1, embodied as an implantable medical device (IMD).

9. The system of claim 1 wherein the processor is programmed to employ curve fitting between the first point of the monitored aortic pressure and the first point of the measured left atrial pressure to thereby interpolate left ventricular pressure during isovolumic contraction.

10. The system of claim 1 wherein the processor is programmed to employ curve fitting between the second point of the monitored aortic pressure and the second point of the measured left atrial pressure to thereby interpolate left ventricular pressure during isovolumic relaxation.

11. The system of claim 1 wherein the first point of the monitored aortic pressure coincides with a transition from declining aortic pressures to increasing aortic pressures.

12. The system of claim 1 wherein the cardiac valve event comprises heart sounds and the first point of the monitored aortic pressure coincides with the end of the S1 heart sound.

13. The system of claim 1 wherein the first of the monitored cardiac valve events comprise the S1 heart sound.

14. The system of claim 1 wherein the first of the monitored cardiac valve events comprise the peak of the R wave.

15. The system of claim 1 wherein the second of the monitored cardiac valve events comprises the S3 heart sound.

16. A system for interpolating left ventricle pressure in a patient comprising:
   at least one sensor configured to sense blood pressures downstream of the patient's left ventricle, wherein the at least one sensor is specifically configured to provide a first point and a second point of a waveform corresponding to an aortic pressure measurement; and
   a processor programmed to receive blood pressures from the at least one sensor, to identify the first point and the second point on the waveform corresponding to an aortic pressure curve defined by the sensed blood pressures, wherein the first point coincides with a transition from declining aortic pressures to increasing aortic pressures, and the second point coincides with a sudden transition from declining aortic pressures of a first negative slope to declining aortic pressures of a second negative slope less than the first negative slope, and to employ curve fitting to approximate left ventricular pressure from a plurality of the sensed blood pressures subsequent to the first point and prior to the second point.

17. The system of claim 16, embodied as an implantable medical device (IMD).

18. The system of claim 16, wherein the at least one sensor is embodied on an implantable medical device (IMD) and wherein the processor is embodied on an external computing device that is configured to receive the sensed blood pressures from the IMD.

19. The system of claim 16, wherein the at least one sensor is embodied as a blood pressure cuff for positioning on or around an extremity of the patient.

20. An implantable medical device (IMD) comprising:
   a first sensor means for obtaining pressure data which defines an aortic pressure of a patient to which the IMD is implanted;
   a second sensor means for obtaining event data relating to opening and closing of the patient's mitral valve and aortic valve, wherein the event data corresponds to a first point and a second point on a waveform corresponding to an aortic pressure curve defined by the pressure data obtained by the first sensor means, wherein the second sensor means for obtaining is configured to identify the first point as a point on the aortic pressure curve that coincides with a transition from declining aortic pressures to increasing aortic pressures, and to identify the second point as a point on the aortic pressure curve that coincides with a sudden transition from declining aortic pressures of a first negative slope to declining aortic pressures of a second negative slope less than the first negative slope; and
   a processor means for interpolating left ventricle pressure from pressure data subsequent to the first point and pressure data prior to the second point.

21. The IMD of claim 20, wherein the first sensor means for obtaining pressure data comprises means for sensing arterial pressure and means for approximating the aortic pressure from the arterial pressure.

22. The IMD of claim 20, wherein the first sensor means for obtaining pressure data comprises means for directly sensing aortic pressure.

23. The IMD of claim 20, wherein the means for interpolating comprises means for curve fitting to the aortic pressure data to approximate a portion of the left ventricle pressure.

* * * * *